United States Patent
Roberts et al.

(10) Patent No.: US 12,249,424 B2
(45) Date of Patent: Mar. 11, 2025

(54) DECISION-SUPPORT TOOLS FOR PEDIATRIC OBESITY

(71) Applicant: CERNER INNOVATION, INC., Kansas City, KS (US)

(72) Inventors: Andrew Roberts, Overland Park, KS (US); Sasanka Are, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 1221 days.

(21) Appl. No.: 16/153,328

(22) Filed: Oct. 5, 2018

(65) Prior Publication Data

US 2019/0108916 A1     Apr. 11, 2019

Related U.S. Application Data

(60) Provisional application No. 62/568,487, filed on Oct. 5, 2017.

(51) Int. Cl.
  *G16H 50/30*     (2018.01)
  *G16H 10/60*     (2018.01)
  (Continued)

(52) U.S. Cl.
  CPC ............. *G16H 50/30* (2018.01); *G16H 10/60* (2018.01); *G16H 20/10* (2018.01); *G16H 20/30* (2018.01);
  (Continued)

(58) Field of Classification Search
  CPC ........ G16H 50/30; G16H 20/30; G16H 40/20; G16H 50/50; G16H 50/60; G16H 20/10; G16H 40/63; G16H 20/60
  See application file for complete search history.

(56) References Cited

U.S. PATENT DOCUMENTS

| | | | |
|---|---|---|---|
| 2008/0294370 A1* | 11/2008 | Kriger | G01G 19/4146 702/173 |
| 2013/0159023 A1* | 6/2013 | Srinivas | G06Q 10/10 705/4 |

(Continued)

FOREIGN PATENT DOCUMENTS

| | | | | |
|---|---|---|---|---|
| DE | 102012100410 | * | 5/2013 | |
| DE | 102012100410 B3 | * | 5/2013 | ............ G01G 19/50 |

OTHER PUBLICATIONS

Flegal et al., "Characterizing Extreme Values of Body Mass Index-for-Age by Using the 2000 Centers for Disease Control and Prevention Growth Charts", Am. J. Clin. Nutr., vol. 90, 2009, pp. 1314-1320.

(Continued)

*Primary Examiner* — Maikhanh Nguyen
(74) *Attorney, Agent, or Firm* — Invoke

(57) ABSTRACT

A decision support method and system is provided for monitoring and treating pediatric obesity. Embodiments include generating obesity risk curves corresponding to obesity risk levels, for example, severe and morbid obesity risk levels. Generating obesity risk curves depends on predicting at least one health proxy such as, for example, spend data and chronic conditions. Generating severe obesity curves depends on an age-dependent multiplier. An obesity risk level is assigned to a target pediatric patient using the obesity risk curves dependent on the age-dependent multiplier. In some aspects, an intervening response is initiated based on the assigned obesity risk level.

33 Claims, 13 Drawing Sheets

(51) Int. Cl.
- *G16H 20/10* (2018.01)
- *G16H 20/30* (2018.01)
- *G16H 20/60* (2018.01)
- *G16H 40/20* (2018.01)
- *G16H 40/63* (2018.01)
- *G16H 50/50* (2018.01)

(52) U.S. Cl.
CPC ............. *G16H 20/60* (2018.01); *G16H 40/20* (2018.01); *G16H 40/63* (2018.01); *G16H 50/50* (2018.01)

(56) References Cited

U.S. PATENT DOCUMENTS

| | | | | |
|---|---|---|---|---|
| 2014/0082627 | A1* | 3/2014 | Manjarekar | G06F 9/5066 718/104 |
| 2014/0162223 | A1* | 6/2014 | Saavedra | G16H 20/60 434/127 |
| 2016/0378942 | A1* | 12/2016 | Srinivas | G16H 50/30 705/2 |
| 2021/0319887 | A1* | 10/2021 | Derrick, Jr. | A61B 5/7275 |

OTHER PUBLICATIONS

Gulati et al., "Clinical Tracking of Severely Obese Children: A New Growth Chart", Pediatrics, vol. 130, No. 6, Dec. 2012, pp. 1136-1140.

* cited by examiner

DECISION-SUPPORT TOOLS FOR PEDIATRIC OBESITY

CROSS-REFERENCE TO RELATED APPLICATIONS

This application claims the benefit of U.S. Provisional Application No. 62/568,487 titled "DECISION-SUPPORT TOOLS FOR PEDIATRIC OBESITY," filed on Oct. 5, 2017, which is hereby expressly incorporated by reference in its entirety.

BACKGROUND

Early detection of obesity, particularly in children, and identification of the level of obesity has been found to be important in the effectiveness of interventions. Pediatric obesity is typically determined using growth charts to compare growth of children relative to a pre-defined population. Because a child's body mass index (BMI) is age-dependent, BMI, by itself, is not a good measure of body type for children. Rather, to understand a change in a child's BMI, the BMI is normalized across all ages, and this normalization of BMI is traditionally done by clinicians using percentiles for age. Both the Centers for Disease Control and Prevention (CDC) and the World Health Organization (WHO) have developed growth charts that plot curves for certain percentiles. These curves, however, do not measure severe obesity, and the BMIs for older children are often not even in the range of plottable values in these charts. In addition, efforts to address these deficiencies have relied on constant-multipliers rather than age-dependent multipliers for plotting curves in growth charts. As such, efforts to address these deficiencies of traditional growth charts do not account for growth velocity of children. These deficiencies lead to underdiagnosing of severe obesity in younger pediatric patients and, consequently, inability to effectively intervene.

SUMMARY

Systems, methods, and computer-readable media are provided for decision support for monitoring and treating obese pediatric patients. In particular, a system is provided for generating obesity risk curves for pediatric patients based on an age-dependent multiplier. Some embodiments of the present disclosure may include the generated severe curves based on an age-dependent multiplier that is formed, in part, with a growth velocity value and a threshold risk level. An obesity risk level is assigned to a target pediatric patient using the obesity risk curves. One or more intervening actions are initiated based on the assigned obesity risk level.

One aim of the disclosure is to provide an accurate and up-to-date representation of obesity in pediatric patients and, in some aspects, notify a caregiver of the target pediatric patient. Conventional systems rely on constant-multipliers, rather than age-dependent multipliers, and do not account for the growth velocity of children. By utilizing an age-dependent multiplier and a growth velocity value, decision support applications utilizing obesity risk curves generated in accordance with the present disclosure are more accurate. For instance, once an obesity curve is generated and used to assess an obesity level of a pediatric patient, a caregiver may be notified. Some embodiments may automatically modify computer code executed in a healthcare software program for treating a patient or scheduling services or other healthcare resources for the patient. Additionally, the obesity risk level assigned may be used in conjunction with the severe obesity curves to optimize pediatric patient care and to increase the likelihood of better outcomes in the future.

BRIEF DESCRIPTION OF THE DRAWINGS

The present invention is described in detail below with reference to the attached drawing figures, wherein.

DETAILED DESCRIPTION

Figure 1A:
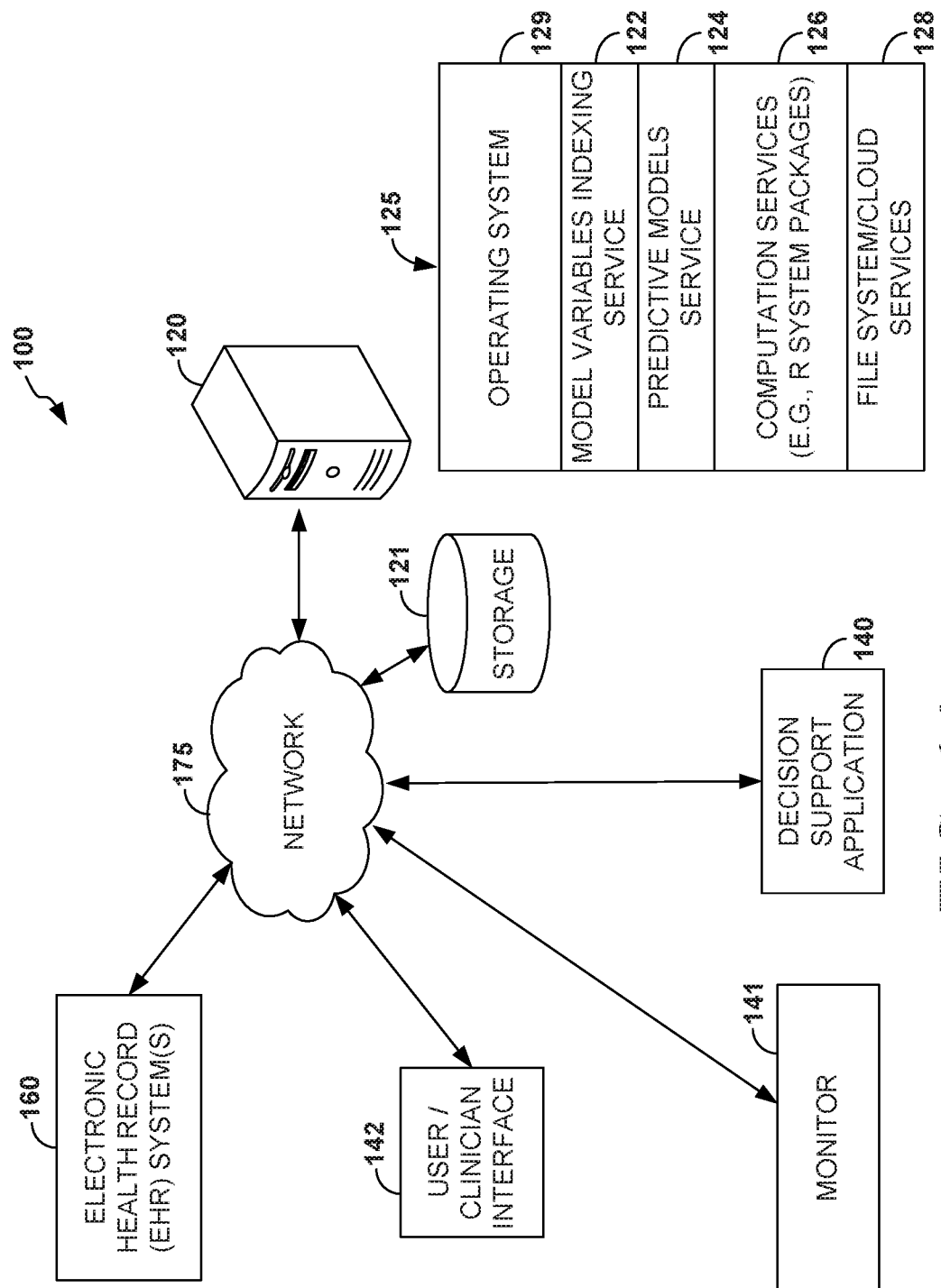
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, this disclosure describes, among other things, systems, methods, and computer-readable media assigning pediatric obesity levels (also referred to herein as obesity risk levels) to pediatric patients based on age-dependent pediatric growth curves. Specifically, age-dependent multipliers are used to extrapolate a $95^{th}$ Percentile curve to provide accurate detections of varying levels of obesity. In some embodiments, the age-dependent multipliers are computed using variable values that are determined by training a predictive model to forecast health proxies for obesity. Further, the detected level of obesity may be used for initiating intervening actions for the pediatric patients. Accordingly, in some embodiments, the methods and systems may be implemented as a decision support computer application or tool and may be part of a more comprehensive healthcare decision support application for monitoring pediatric patients and providing decision support to caregivers. Such decision support technology plays a large role in modern medicine.

Accordingly, embodiments of the technology described herein improve on conventional medical decision support technologies by utilizing improved detection of pediatric obesity levels for initiating intervening actions and, thus, provide a practical application in decision support systems for monitoring and treating obese pediatric patients. Specifically, pediatric obesity is typically determined using growth charts to compare the growth of children relative to a pre-defined population. Unlike with adults, the measure of a child's body mass index (BMI) must be normalized across all ages, and clinicians use percentiles for ages to determine a pediatric body type. Existing methods for assigning a pediatric body type using percentiles either do not provide levels of severe obesity or do not accurately account for growth velocity. These existing methods lead to underdiagnosing of severe obesity in younger children (i.e., younger pediatric patients) and, consequently, impacting the effectiveness of interventions.

Accordingly, one aim of embodiments of this disclosure is to improve upon conventional practice by deriving more accurate assignments of obesity levels to pediatric patients for more effective treatment and care. One improvement upon conventional practice is to more accurately detect higher obesity levels in younger pediatric patients, where it is the most effective to have a correct diagnosis for early intervention and treatment. Additionally, some embodiments of the disclosure include an improved user interface presenting a user with obesity risk curves generated with an age-dependent multiplier that may be used to facilitate diagnosing a pediatric patient with a higher level severity of obesity that would otherwise have gone undetected with conventional user interfaces presenting obesity curves.

Referring now to the drawings in generally and, more specifically, referring to FIG. 1A, an aspect of an operating environment 100 is provided that is suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for pediatric obesity. The operating environment 100 includes one or more electronic health record (EHR) system(s) 160. Examples of EHR system 160 may include, but are not limited to, a hospital EHR system, a health information exchange EHR system, an ambulatory clinic EHR system, and a psychiatry/neurology EHR system. EHR system 160 may be communicatively coupled to a network 175, which is communicatively coupled to a computer system 120. In some embodiments, components of the operating environment 100 that are shown as distinct components may be embodied as part of or within other components of the operating environment 100. EHR system 160 may be implemented in the computer system 120, and EHR system 160 may perform functions for two or more EHR systems (not shown).

The network 175 may comprise the Internet, and/or one or more public networks, private networks, other communications networks such as a cellular network, or similar network for facilitating communication among devices connected through the network 175. In some embodiments, the network 175 may be determined based on factors such as a source and a destination of information communicated over the network 175, a path between the source and the destination, or nature of the information. For example, intra-organization or internal communication may use a private network or a virtual private network (VPN). Moreover, in some embodiments, items shown as being communicatively coupled to the network 175 may be directly communicatively coupled to other items shown communicatively coupled to the network 175.

In some embodiments, the operating environment 100 may include a firewall (not shown) between a first component and the network 175. In such embodiments, the firewall may reside on a second component located between the first component and the network 175, such as on a server (not shown), or may reside on another component within the network 175, or may reside on or as part of the first component.

Embodiments of EHR system 160 may include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts EHR system 160 that may be used for storing and retrieving patient information, it is contemplated that an embodiment of the disclosure relies on a decision support application 140 and/or a monitor 141 (in addition to or in place of EHR system 160) for storing and retrieving patient record information, such as information acquired from the monitor 141.

Example operating environment 100 further includes a provider user/clinician interface 142 communicatively coupled through network 175 to EHR system 160. Although operating environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which obesity risk levels are determined according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders for the patient from the clinician/user based on the results of monitoring and predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, patient decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilizes user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments. As shown in example operating environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables.

In one embodiment, monitor 141 comprises sensors for obtaining (and, in some instances, pre-processing or interpreting) and recording of physiological variables such as BMI, which may be obtained continuously, periodically, or at irregular intervals. In some embodiments, monitor 141 comprises patient bedside monitor, such monitors used in hospital. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about the patient, such as the monitored variables and/or clinical narratives regarding the patient, used according to the embodiment of the invention disclosed herein may be received from a patient's historical data in EHR system 160, or from human measurements, human observations, or automatically determined by sensors in proximity to the patient.

As stated, examples of physiological variables monitored by monitor 141 can include BMI as described herein. Additionally, in some embodiments, monitor 141 may include, other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient to facilitate clinical decision making. In an embodiment, monitor 141 comprises a sensor probe, such as an EEG probe, and a communication link that periodically transmits identification information and probe data to decision support application 140 so that the time series of monitored values is stored and accessed by application 140, enabling application 140 to form an alarm indication and/or a physiological variable decision statistic. In an embodiment, application 140 facilitates the collection of raw sensor information, which may be received from monitor 141, and performs signal processing and computations thereby forming a physiological variable decision statistic, cumulative summing, trending, wavelet processing, thresholding, computational processing of decision statistics, logical processing of decision statistics, pre-processing or signal condition, etc., part or all of which may be performed on monitor 141, application 140, and/or computer system 120.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting application 140 for performing signal conditioning of the measured patient variable(s). In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting health proxies based on obesity risk level and age, which, in some embodiments, are used to determine severe obesity scores for pediatric growth charts.

Computation services 126 perform statistical software operations as described herein. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing one or more models, including logistic models.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer-storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
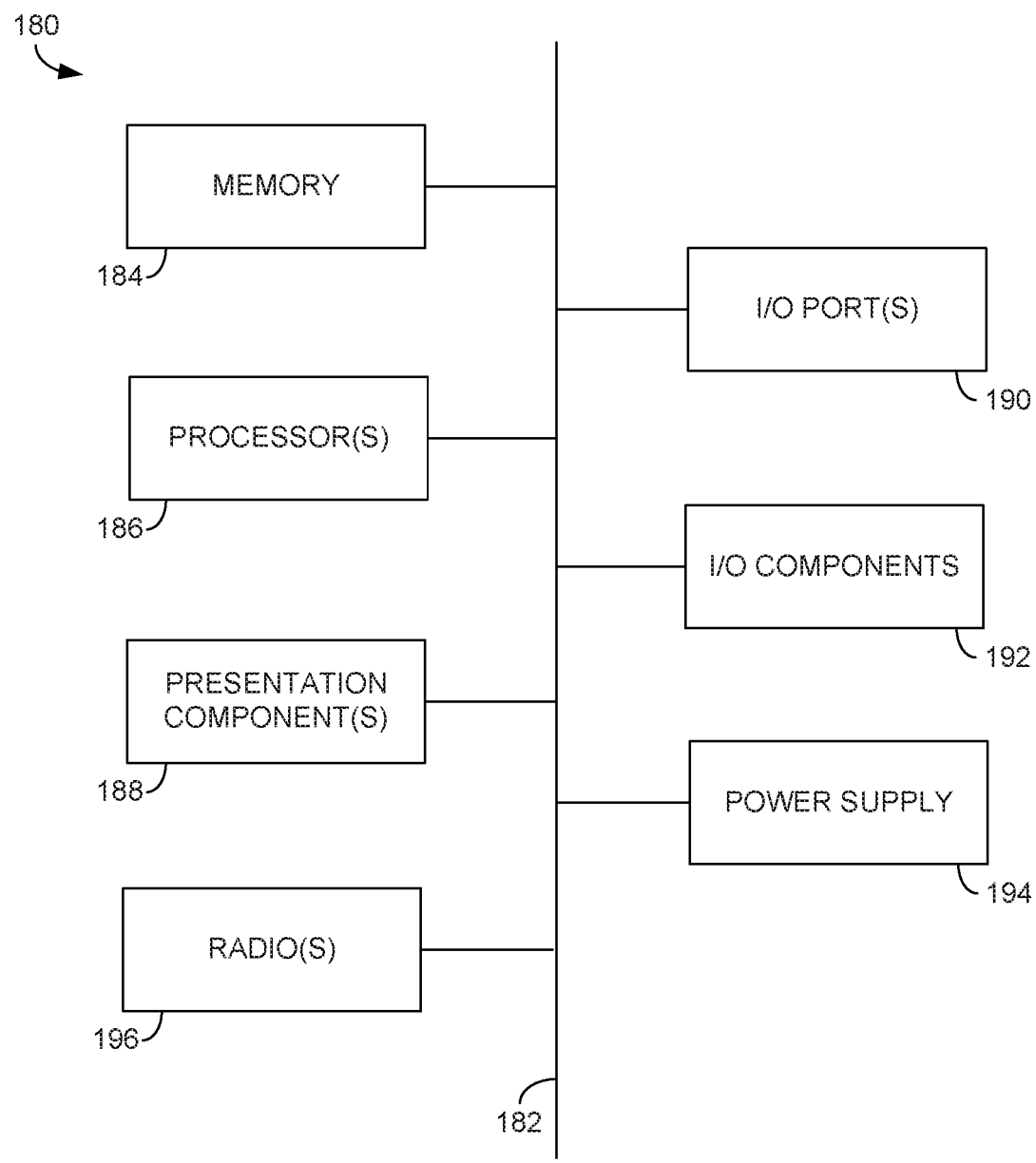

Turning briefly to FIG. 1B, there is shown one example embodiment of computing system 180 representative of a system architecture that is suitable for computer systems such as computer system 120. Computing system 180 includes a bus 182 that directly or indirectly couples the following devices: memory 184, one or more processors 186, one or more presentation components 188, one or more input/output (I/O) ports 190, one or more input/output components 192, an illustrative power supply 194, and one or more radios 196. Bus 182 represents what may be one or more buses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 184 includes computer-storage media in the form of volatile and/or nonvolatile memory. The memory may be removable, non-removable, or a combination thereof. Exemplary hardware devices include, but are not limited to, solid-state memory, hard drives, optical-disc drives, etc. Computing system 180 includes one or more processors that read data from various entities, such as memory 184 or I/O component(s) 192. Presentation component(s) 188 present data indications to a user or other device. Presentation component(s) 188 may include, but are not limited to, a display device, speaker, printing component, vibrating component, etc.

In some embodiments, computing system 180 comprises radio(s) 196 that facilitates communication with a wireless-telecommunications network. Illustrative wireless telecommunications technologies include CDMA, GPRS, TDMA, GSM, and the like. Radio(s) 196 may additionally or alternatively facilitate other types of wireless communications including Wi-Fi, WiMAX, LTE, or other VoIP communications. As can be appreciated, in various embodiments, radio(s) 196 can be configured to support multiple technologies and/or multiple radios can be utilized to support multiple technologies.

I/O port(s) 190 allow computing system 180 to be logically coupled to other devices, including I/O component(s) 192, some of which may be built in. Illustrative components include a microphone, joystick, game pad, satellite dish, scanner, printer, wireless device, etc. The I/O component(s) 192 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
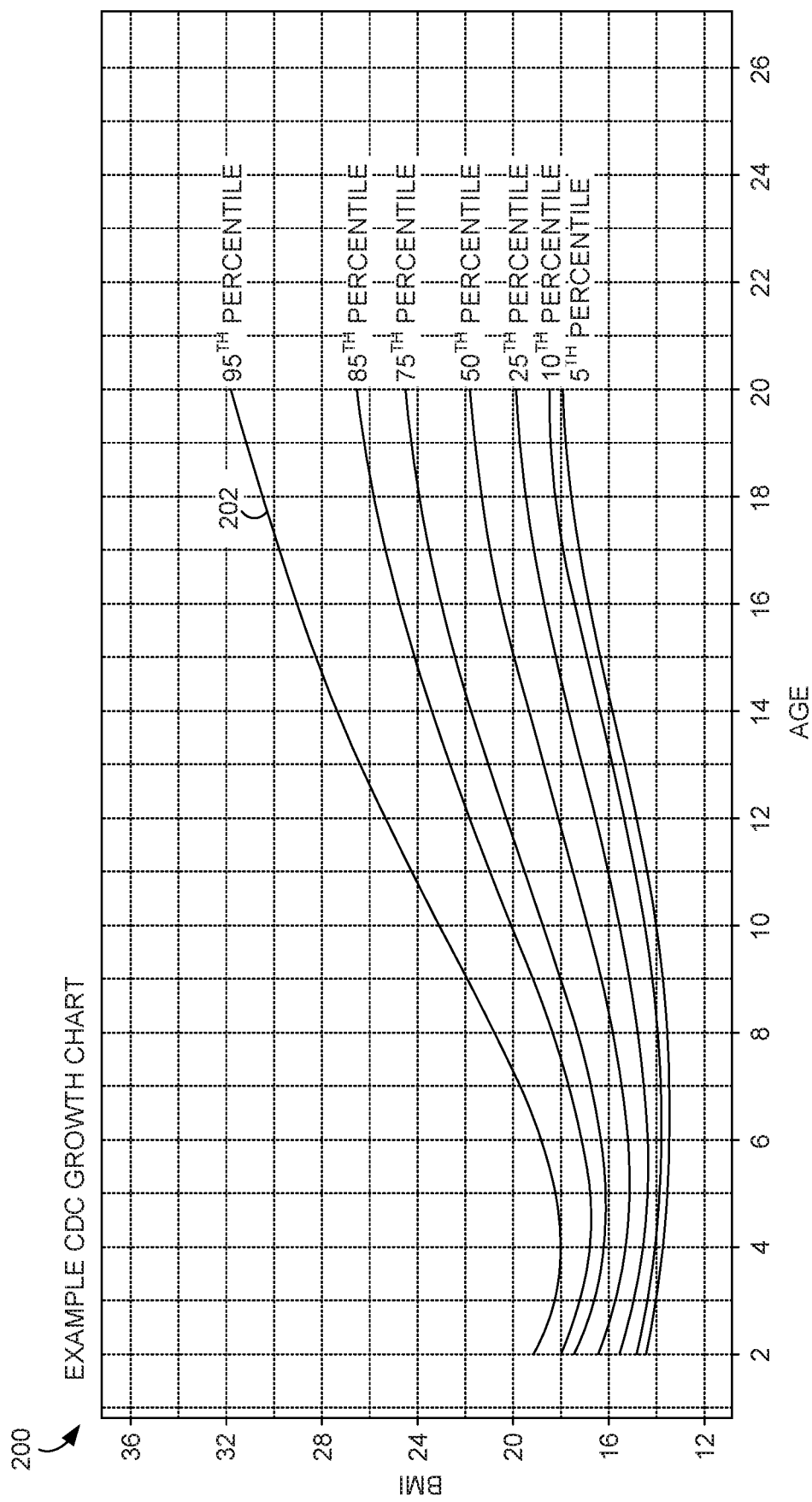
FIGS. 2-4 depict examples of pediatric growth charts in accordance with conventional methods for determining pediatric obesity.
Figure 3:
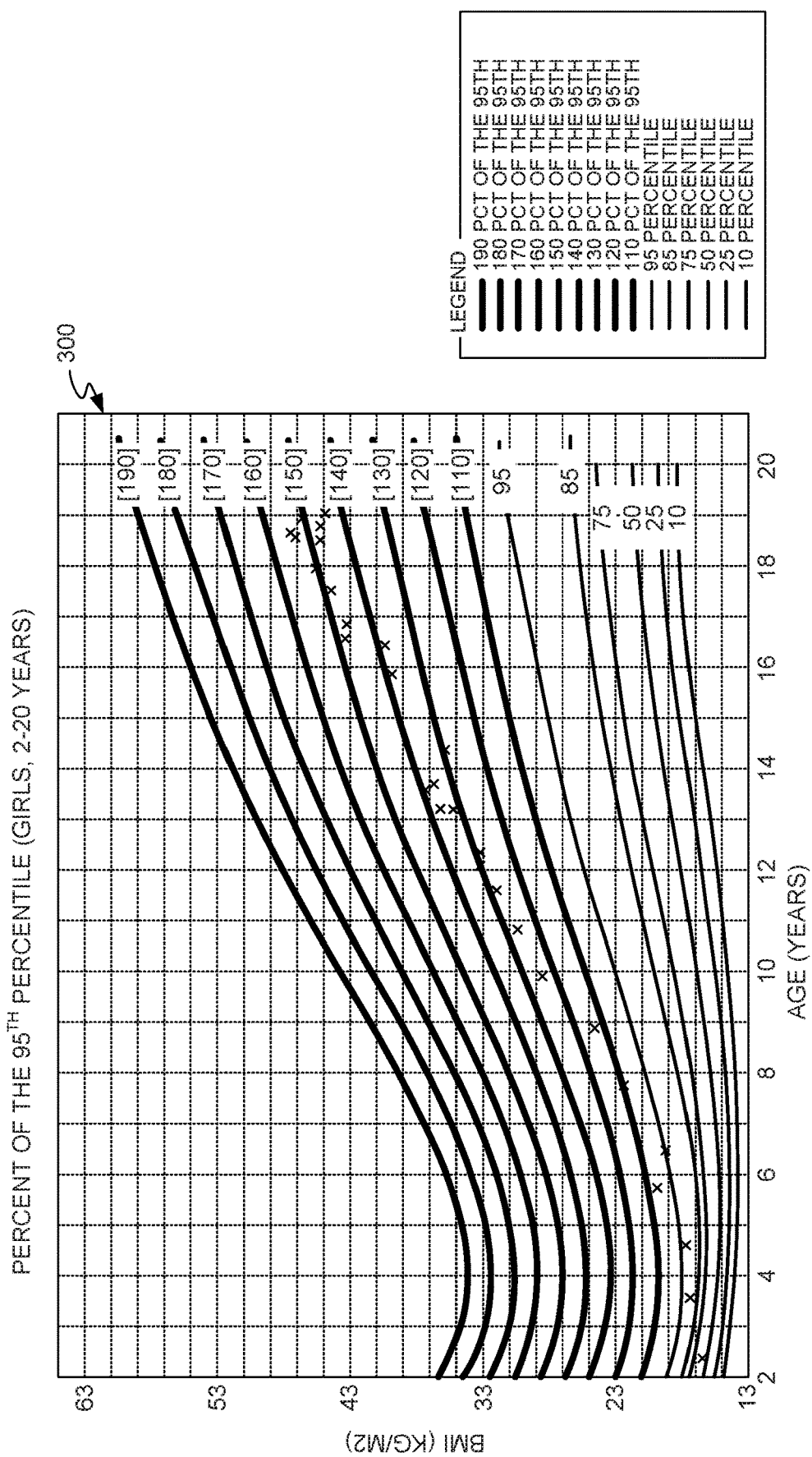
Figure 4:
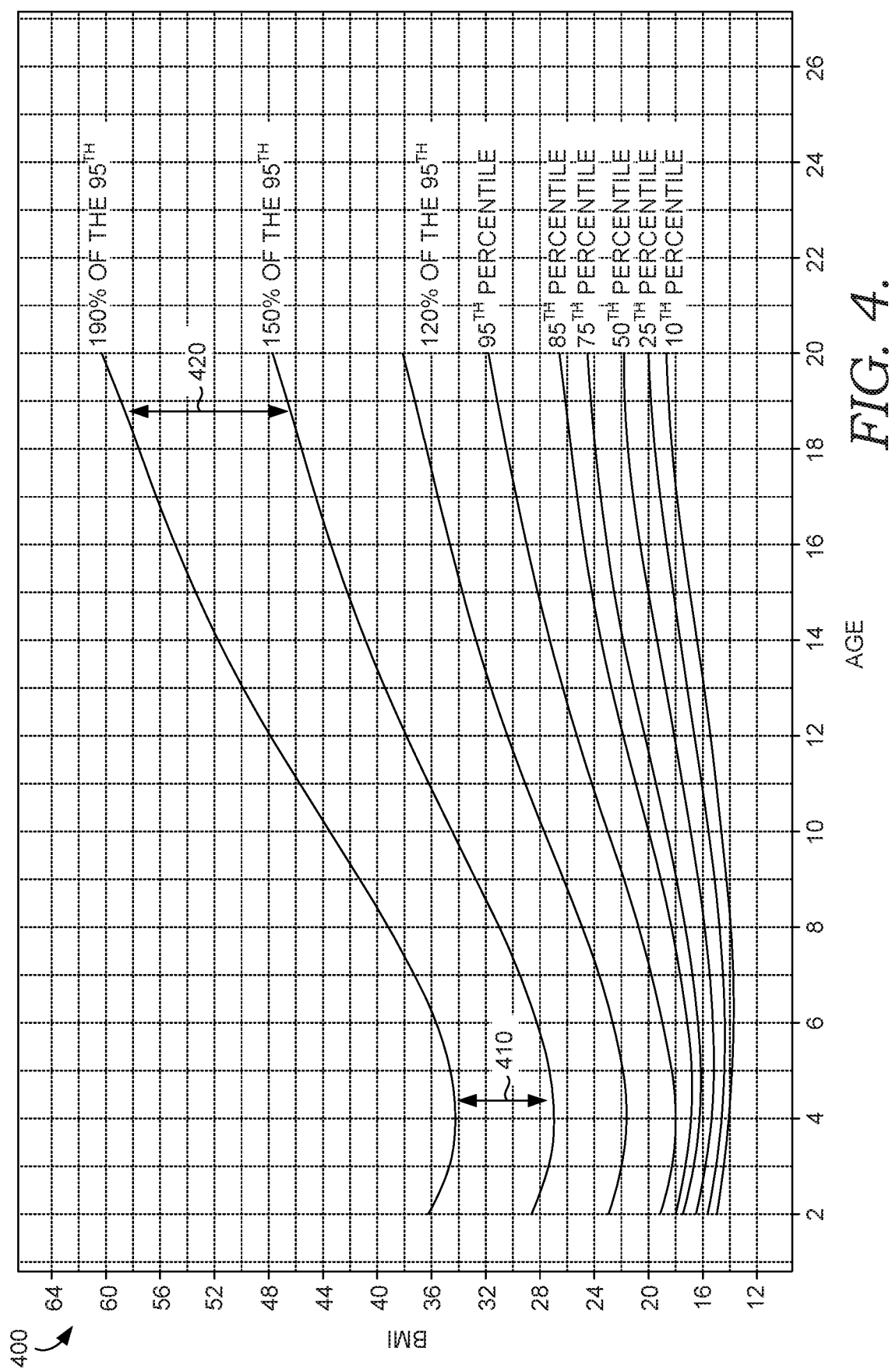

Turning to FIGS. 2-4, pediatric growth curves determined under conventional methods are discussed herein with respect to limitations in assigning obesity levels and initiating effective intervening actions. As previously mentioned, pediatric obesity is more difficult to accurately identify than adult obesity. Generally, obesity in adults is defined as having a BMI over 30. This definition is not age-dependent. For adults, the CDC also provides a method to categorize the severity of obesity (e.g., severe obesity, morbid obesity). Pediatric obesity, on the other hand, is age-dependent because a child's BMI is age-dependent. As such, using only BMI as a measure of body type for children is not accurate for diagnosing obesity.

To normalize BMI across ages to provide an obesity diagnosis, clinicians traditionally utilize percentile for age. Both the CDC and the WHO have developed growth charts that plot curves for certain percentiles. The curves plotted in the growth charts are not empirical percentiles of the population; rather, they are smoothed approximations.

FIG. 2 depicts an example CDC growth chart 200, which measures percentiles of BMI across an age range. The percentile curves, such as $95^{th}$ Percentile curve 202, in CDC growth chart 200 are based on a pre-defined population. Rather than identifying body type directly from BMI, the curves associated with each percentile identified are used to identify a child's body type, such as underweight, healthy weight, overweight, and obese. The table provided below demonstrates how body type in adults and children are traditionally categorized.

| Body Type | Adults | Children |
| --- | --- | --- |
| Underweight | BMI < 18.5 | BMI for age < $5^{th}$ Percentile |
| Healthy Weight | 18.5 < BMI < 25 | $5^{th}$ Percentile < BMI for age < $85^{th}$ Percentile |
| Overweight | 25 < BMI < 30 | $85^{th}$ Percentile < BMI for age < $95^{th}$ Percentile |
| Obese | 30 < BMI < 35 | $95^{th}$ Percentile < BMI for age |
| Severely Obese | 35 < BMI < 40 | N/A |
| Morbidly Obese | 40 < BMI < 50 | N/A |
| Super Obese | 50 < BMI | N/A |

The highest percentile curve traditionally illustrated in pediatric growth charts like the one CDC growth chart 200 is the $95^{th}$ Percentile curve, and any BMI above the $95^{th}$ Percentile curve is traditionally defined as "obese" for children. Accordingly, these conventional charts from health organizations like the CDC do not account for different types of obesity for pediatric patients and, therefore, do not define severe obesity, morbid obesity, or super obesity for pediatric populations in the same way as defined for adults.

Clinicians have, nevertheless, traditionally used an approximate $99^{th}$ Percentile curve as an indicator of severe pediatric obesity. However, the curve for the approximate $99^{th}$ Percentile cannot be accurately produced using the same methods as the curves on the standard pediatric growth chart shown in CDC growth chart 200. The $99^{th}$ Percentile curve used is an extrapolated curve that differs from the empirical curve by some degree. For example, the standard approximated curve for the $99^{th}$ Percentile differ from the empirical curve by an average of two BMI units for girls. Additionally, older children often have a BMI value that is not even with the range of values that can be plotted within the growth chart, eliminating the chance for even a visual representation of the severity of obesity. In other words, even if a BMI value being off the chart indicates severe obesity, it does not provide an indication of the severity of the severe obesity (e.g., severe obesity, morbid obesity, or super obesity).

In light of the deficiencies of the standard pediatric growth charts and definitions, there have been prior efforts to quantify severe pediatric obesity to stratify groups of pediatric obesity by taking constant multiples (e.g., 1.1, 1.2, 1.3, etc.) of the $95^{th}$ Percentile curve. Generally, the "120 Percent of the $95^{th}$ Percentile" curve ($95^{th}$ Percentile curve multiplied by 1.2) is generally used as the approximation for the $99^{th}$ Percentile to identify severe pediatric obesity. For example, turning to FIG. 3, a pediatric growth chart 300 is depicted using this method. Pediatric growth chart 300 includes the constant multiples of the $95^{th}$ Percentile, including the 120 Percent of the $95^{th}$ Percentile curve. This approach (and the resulting chart depicted in FIG. 3) has several drawbacks, however. First, a constant-multiplier approach (using constant multiples of the $95^{th}$ Percentile curve) is not age-dependent. For example for a four year-old, the difference between the $10^{th}$ Percentile and $85^{th}$ Percentile is about 2.5 units; the difference between overweight ($85^{th}$ Percentile) and obese ($95^{th}$ Percentile) is about 0.75 units; and the difference between the $95^{th}$ Percentile and "120 Percent of the $95^{th}$ Percentile" is about 4 units. In contrast, for an eighteen year-old those differences are 8 units, 4.5 units, and 6 units, respectively. In other words, the constant-multiplier approach does not account for the growth velocity of children. Based on the relative differences in these units between the eighteen year-old and the four year-old, the using the 120 Percent of the $95^{th}$ Percentile as a threshold for severe obesity is not accurate for pediatric patients, at least at younger ages. Using this inaccurate threshold results in underdiagnosing severe obesity in younger pediatric patients and, consequently, an inability to effectively intervene.

Another drawback of the pediatric growth chart 300 is the number of curves plotted in the obesity range. As illustrated in FIG. 3, the pediatric growth chart 300 created with the constant-multiplier approach leads to nine additional curves concentrated in a small range above the $95^{th}$ Percentile curve. As approximately 84% are not obese (i.e., are overweight, healthy, or underweight), the number of constant-multiplier curves representing obesity with this approach is disproportionate from the actual percentage of pediatric populations falling within those areas. Instead, a more practical approach would be to generate and utilize a chart in which each curve on the chart is meaningful in helping a child, caregiver, or clinician understand the possible risks associated with that child's BMI.

Even after taking away some of the curves, however, the remaining curves created using the constant-multiplier approach are still not accurate. Specifically, the spread between curves appears to be inaccurate as the ratio of BMIs between curves do not seem to be age-dependent. For instance, FIG. 4 illustrates a pediatric growth chart 400 with three constant-multiplier curves to show levels of obesity using 120 Percent of the $95^{th}$ Percentile, 150 Percent of the $95^{th}$ Percentile, and 190 Percent of the $95^{th}$ Percentile. As illustrated, the variance between the 190 Percent of the $95^{th}$ Percentile curve and the 150 percent of the $95^{th}$ Percentile curve for younger ages (as shown by arrow 410) does not appear to be much smaller than the variance between the two curves at older ages (as shown by arrow 420). Rather, there is a wide variance between these curves that extends across all age groups. In this way, even removing some of the constant-multiplier curves, the pediatric growth chart 400 created with constant-multiplier curves does not capture an appropriate obesity risk level for the younger age group and, thereby, still presents the problem of underdiagnosing the more severe forms of obesity. Because diagnosing obesity when patients are younger is often associated with more effective care plans and improved conditions, underdiagnosing at these younger ages is a significant limitation.

Figure 5:
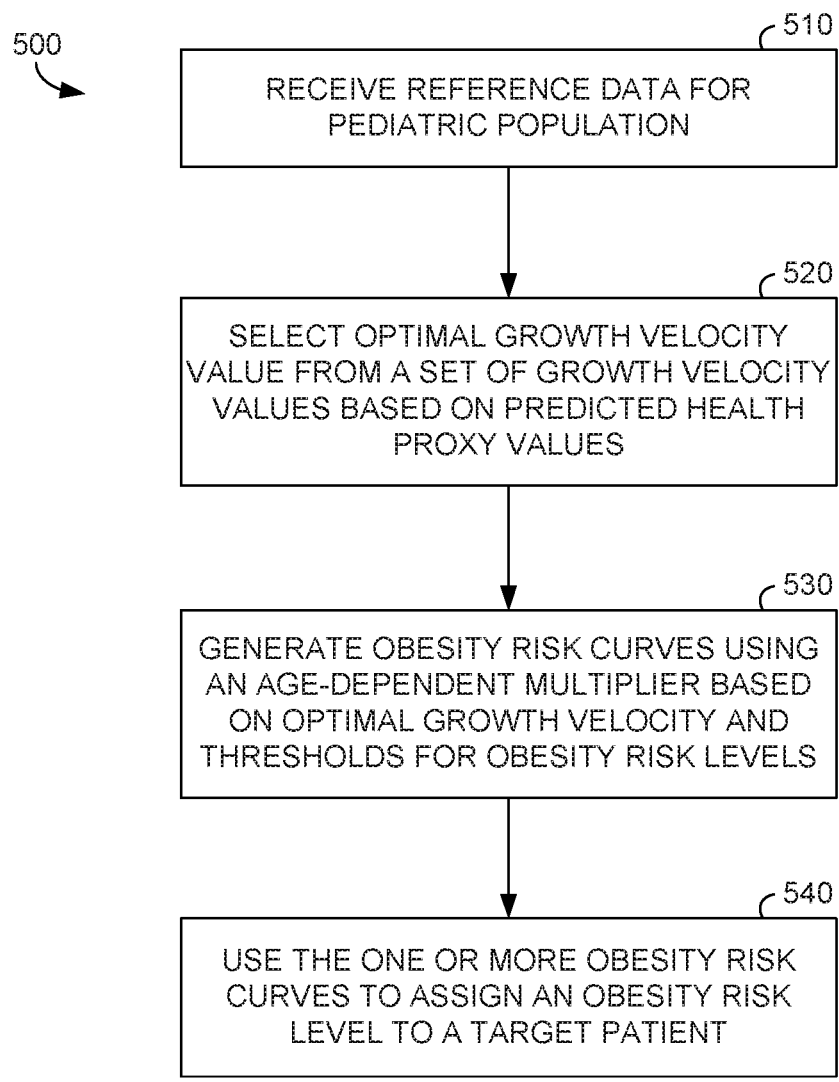
FIG. 5 depicts a flow diagram of a method for providing a decision support system for pediatric obesity, in accordance with an embodiment of the disclosure.

Accordingly, embodiments of this disclosure solve these problems and improve upon the prior, conventional techniques by providing a decision support tool based on a more accurate quantification of severe pediatric obesity. Turning to FIG. 5, a flow chart illustrating an example embodiment of a method for determining pediatric obesity is provided and is referred to generally as method 500. Each block of method 500 and other methods described herein, including methods 1000 of FIG. 10, comprises a computing process that may be performed using any combination of hardware, firmware, and/or software. For instance, various functions may be carried out by a processor executing instructions stored in memory. The methods may be provided by a standalone application, a service or hosted service (either standalone or in combination with another hosted service), or a plug-in to another product, for example. It is further contemplated that the methods may comprise additional steps and that, unless where otherwise indicated, the steps may be performed in alternative orders.

In particular, method 500 utilizes a series of actions taken to generate obesity risk level curves for assigning an obesity risk level to a pediatric patient and initiating an intervening action based on the assigned obesity risk level. In some embodiments, method 500 is suitable for implementation as a computer-performed decision support tool or application for assigning the obesity risk level to pediatric patients. Method 500 facilitates a more accurate diagnosis of severe obesity in pediatric patients compared to conventional methods that, for example, use constant-multipliers in the decision process of determining obesity risk levels.

In accordance with method 500, at step 510, a plurality of reference data for a pediatric population is received. The reference data may comprise measurements for physiological variables (which may also be referred to herein as observable dependent variables). Such physiological variables may include height, weight, BMI, and age. Patient data may also include health proxies, such as spend data or diagnoses of chronic conditions, for example.

The reference data for the pediatric population may be collected in different ways, including, but not limited to, family doctor visits, remote monitoring devices, remote technology, and smart technology. The data, such as the physiological variable data, may be received from an EHR, such as a medical EHR within EHR system 160 in FIG. 1, associated with a pediatric patient within the population or from other data storage, or may be received directly from a monitoring device, such as patient monitor 141. Reference data may further be retrieved from claims data or databases associated with benefit providers and payors. The reference data may be received continuously or periodically. Further, the reference data for the pediatric population may include data already recorded and stored within a predetermined time frame, such as the past five years.

At step 520, an optimal growth velocity value is selected from a set of possible growth velocity values. In exemplary aspects, the optimal growth velocity value is selected by first normalizing values of BMI for age. The BMI values and age values are determined from the reference data, and the BMI values are normalized for age for each growth velocity value that is within the set because each growth velocity value within the set is being evaluated as a potential optimal growth velocity value. In exemplary embodiments, normalizing BMI values for age is done with the following:

$$V = x^{\left[b + \frac{Age}{20}(1-b)\right]} \times (95th \text{ Percentile})$$

where V is BMI value, b is the growth velocity value, and x is threshold for a new risk category (e.g., such as a level of obesity or percentile). The "95th Percentile" in the equation above represents the commonly known $95^{th}$ percentile curve utilized in conventional pediatric obesity charts. As V and Age values come from the reference data, and b is one of the values from the set of growth velocity values, the above equation is used to solve for x to normalize BMI.

Then, for each growth velocity value, at least one health proxy may be predicted. In exemplary aspects, the health proxy is a measure indicating a level of health for an individual within the pediatric population. Health proxy may comprise health care spend for an individual in the pediatric population or a number or presence of chronic conditions with which the individual has been diagnosed. Health proxy values may be predicted across multiple ages and BMI values for each growth velocity value within the set. The health proxy values may be determined using a quantile regression model, but it is contemplated that alternative predictive models may be used.

Figure 6:
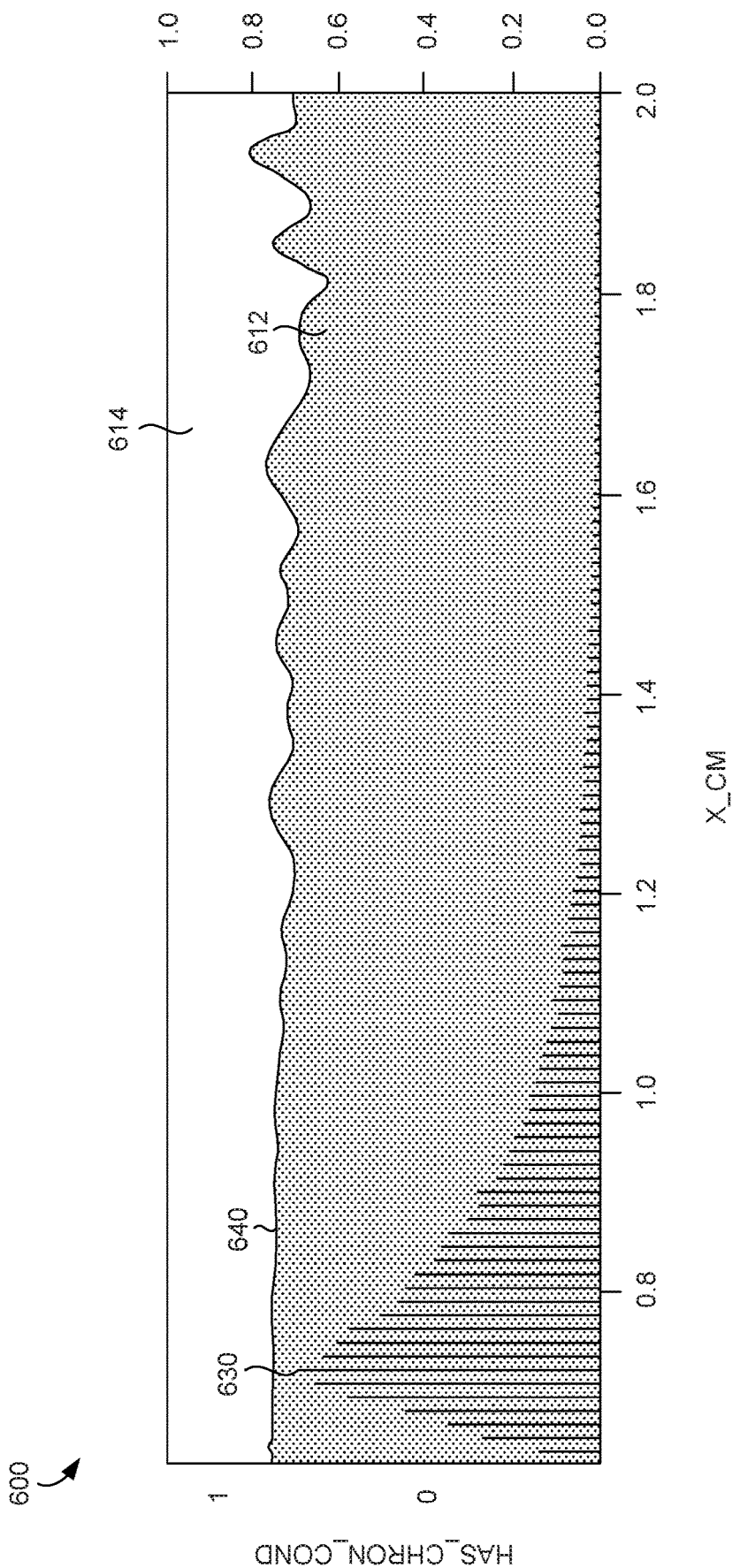
FIG. 6 depicts a graphical illustration of a frequency of female pediatric patients with at least one chronic condition as a function of obesity level in accordance with an embodiment the disclosure.

After predicting health proxy values, such as health care spend or chronic conditions, an optimal growth velocity value may be identified to minimize the dependence of age on the health proxy values. Identifying the growth velocity value that that results in the least dependence of age on the health proxy may be done using smoothed condition frequency. For example, FIG. 6 depicts a graphic illustration 600 of a smoothed conditional frequency of female pediatric patients with at least one chronic condition as a function of x. The dotted region 612 corresponds to 0 on the left Y-axis, indicating a pediatric individual from the reference population has no chronic conditions. The unshaded region 614 corresponds to a value of 1 on the left Y-axis, indicating a pediatric individual at least one chronic condition. Values on the right Y-axis indicate conditional probability of an individual having no chronic conditions. The overlaid bars 630 provide a histogram for the corresponding x values, which are thresholds for risk levels. Values of x greater than 1 indicate a form of obesity.

This graphic illustration 600 is based on an example embodiment reduced to practice. In this embodiment, x and b values were optimized using a data set of a population of 65,928 boys and 64,922 girls between 2-20 years old, with a BMI recorded in 2016. Within this population, 16,314 boys were obese and 12,271 girls were obese. In this embodiment, age and BMI were assumed to be the only observable dependent variables. The graphic illustration 600 depicts a smooth conditional frequency based on the growth velocity value (b) being ⅓. As illustrated at the interface between regions 612 and 614 (depicted as line 640), when b=⅓, the probability of a female pediatric patient having at least one chronic condition is approximately linear in x. The growth velocity value of ⅓ was determined to yield a minimal dependence of the health proxy on age in this example embodiment. As such, in some aspects, the optimal growth velocity value is identified as ⅓. It is contemplated that the optimal growth velocity value may be identified as a different value based on different data. Accordingly, the optimal growth velocity value may be updated as more reference data is received to obtain the most accurate selection for the growth velocity value.

Once an optimal growth velocity value is selected, at step 530, one or more obesity risk curves are generated using an age-dependent multiplier. The one or more obesity risk curves measure threshold values of BMI by age for one or more obesity risk levels. For example, obesity risk levels may include severe obesity, morbid obesity, or super obesity; comparable to obesity risk levels previously defined for adults.

Each obesity risk curve is generated using the following calculation that was previously used to normalize BMI values:

$$V = x^{\left[b + \frac{Age}{20}(1-b)\right]} \times (95th \text{ Percentile})$$

Accordingly, $$x^{\left[b + \frac{Age}{20}(1-b)\right]}$$

is the age-dependent multiplier that is based on a set threshold risk value (x), age, and the selected optimal growth velocity value. Each obesity risk curve is associated with a specific threshold risk value, but the optimal growth velocity value remains the same for each curve generated.

In exemplary embodiments, a risk stratification is be performed to determine the x values by selecting values that indicate significant increases in obesity risk level. In one embodiment, the risk stratification may be considered by proportion of the obese population in each category. In another embodiment, x values indicating significant increases may be determined to be 1.2 and 1.5. In yet another embodiment, in addition to the 1.2 and 1.5 values for x, more x values may be used, such as x=1.9. Alternatively, different x values may be used in another embodiment.

The age-dependent multiplier is multiplied with an existing risk curve representing a lower risk level, such as the 95th Percentile curve, to generate a new obesity risk curve. For each curve, x and b remain constant, but age values will change, resulting in the multiplier that is ultimately used for a specific threshold risk level to change with age. In other words, the resulting obesity risk curve created in accordance with embodiments of the disclosure is not a simple multiple of an existing curve (such as the 95th Percentile curve) but, rather, may have a different slope and shape that more accurately defines appropriate obesity levels for pediatric patients.

Figure 7A:
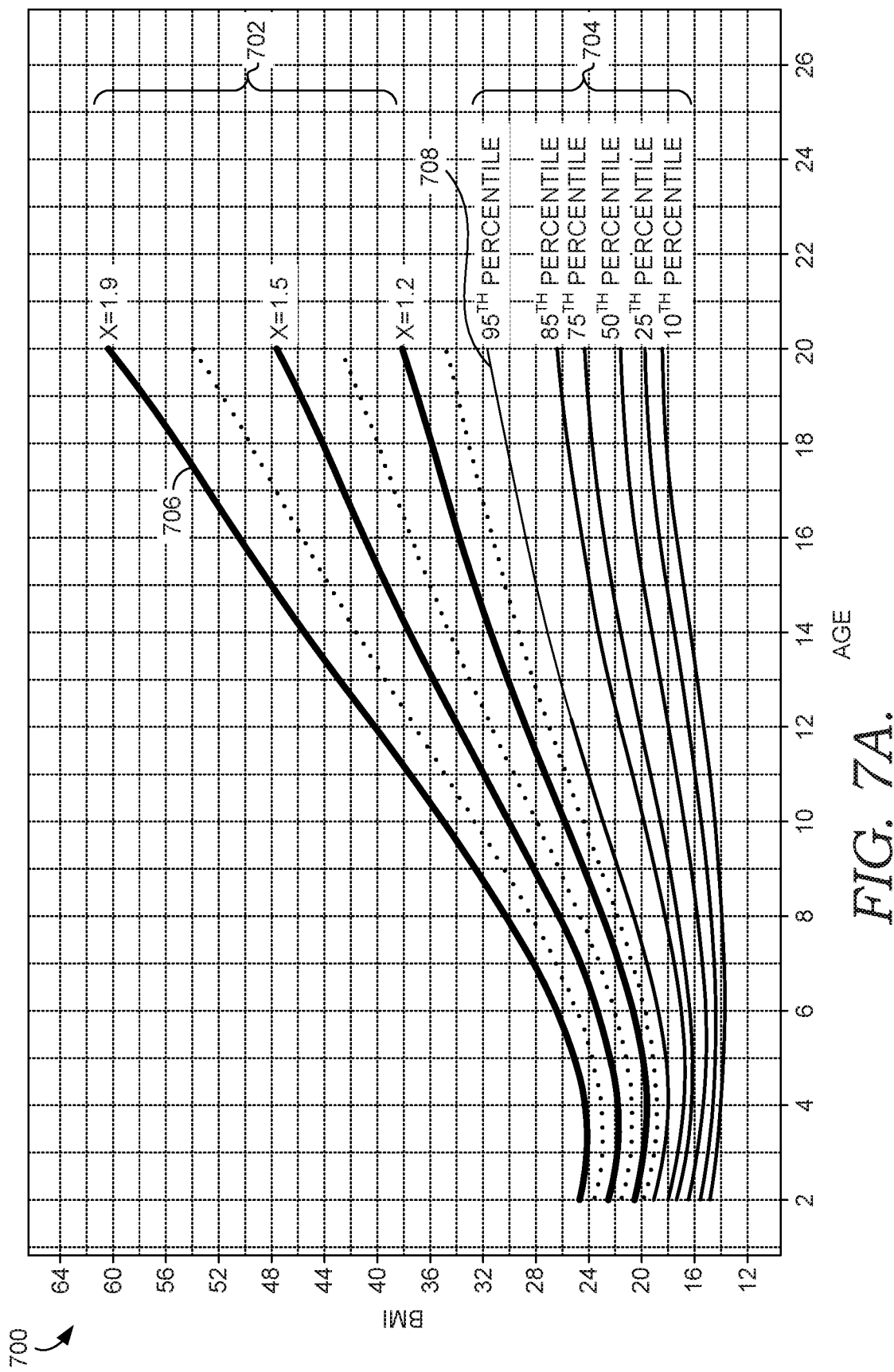
FIGS. 7A and 7B depict graphical illustrations of pediatric growth curves with obesity risk curves determined in accordance with an embodiment of the disclosure.

Turning to FIG. 7A, an improved pediatric growth chart 700 created in accordance with embodiments of the disclosure is provided. The improved pediatric growth chart 700 includes a plurality of traditional percentile curves 704 (the $95^{th}$, $85^{th}$, $75^{th}$, $50^{th}$, $25^{th}$, and $10^{th}$ Percentile curves) reflecting the traditional curves as defined by the CDC. Curve 708, for instance, represents the traditional 95th Percentile curve defined by the CDC. The improved pediatric growth chart 700 also includes a plurality of obesity risk curves 702 that are plotted utilizing a risk stratification dependent upon age. In this example, using b=⅓, the solid curves are based on a risk stratification resulting in x values equal to 1.2, 1.5, and 1.9. Curve 706, for instance, is the age-dependent multiplier of the $95^{th}$ Percentile curve 708 with the age-dependent multiplier being based on a threshold risk value of 1.9. In some embodiments, risk stratification may be done with additional, intermediate obesity risk curves with other x values, such as 1.1, 1.35, and 1.7. The dotted curves illustrated in the improved pediatric growth chart 700 represent these additional intermediate obesity risk curves.

Figure 7B:
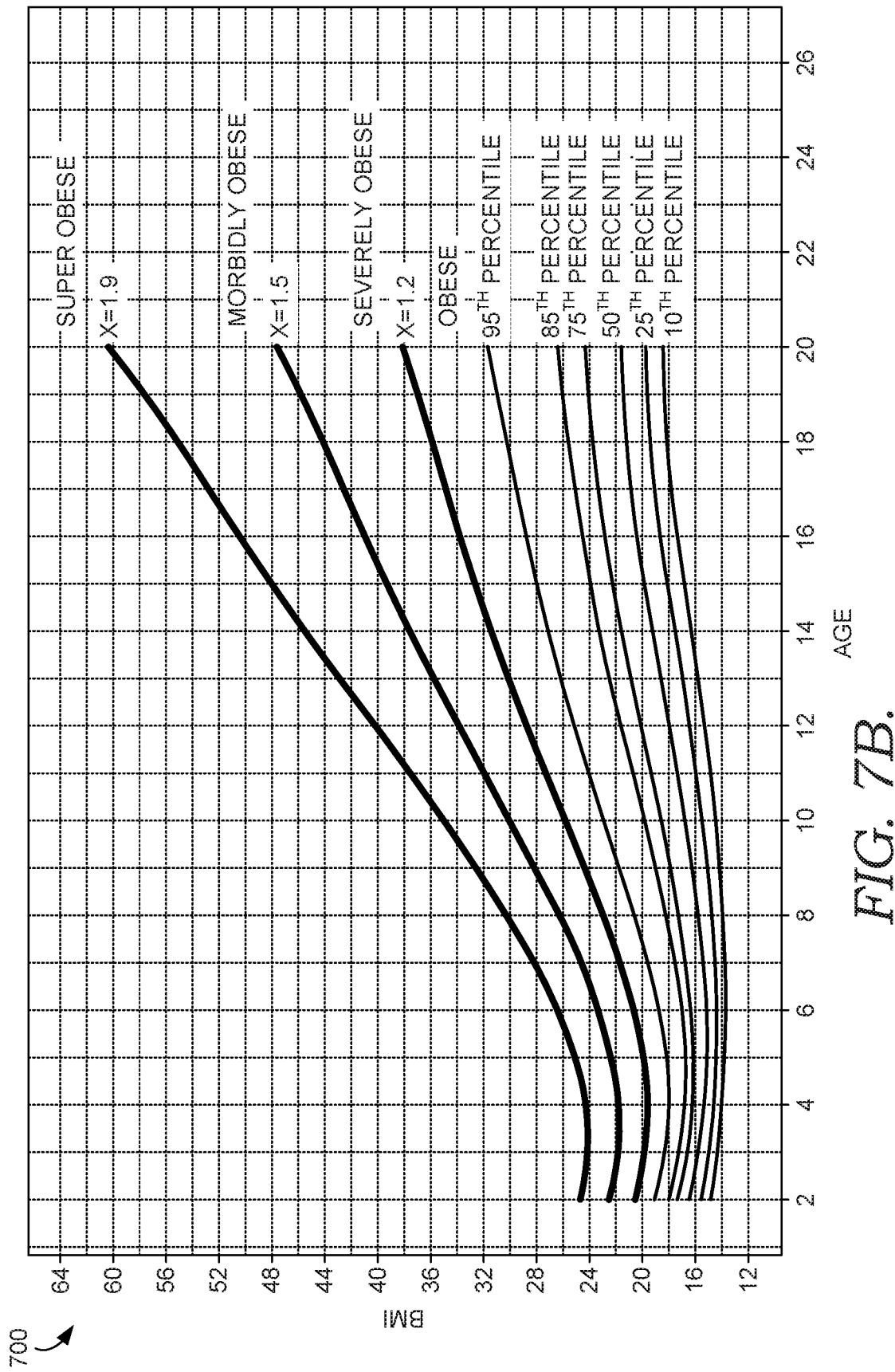

In exemplary embodiments, only three obesity risk curves are created to define three obesity risk levels. For instance, in some aspects, the area between the $95^{th}$ Percentile curve and the x=1.2 curve represents an "obese" level; the area between the x=1.2 curve and the x=1.5 curve represents a "severely obese" level; the area between the x=1.5 curve and the x=1.9 curve represents a "morbidly obese" level; and the area above the x=1.9 curve represents a "super obese" level. It is contemplated that these levels may also be referred to by obese categories 1-4. FIG. 7B illustrates the improved pediatric growth chart 700 without the intermediate curves to show these obesity levels. As illustrated in FIG. 7B, the difference between two adjacent obesity curves, such as the curve at x=1.9 and the curve at x=1.5, is much smaller at younger ages than the difference between the two adjacent curves at older ages.

Figure 8:
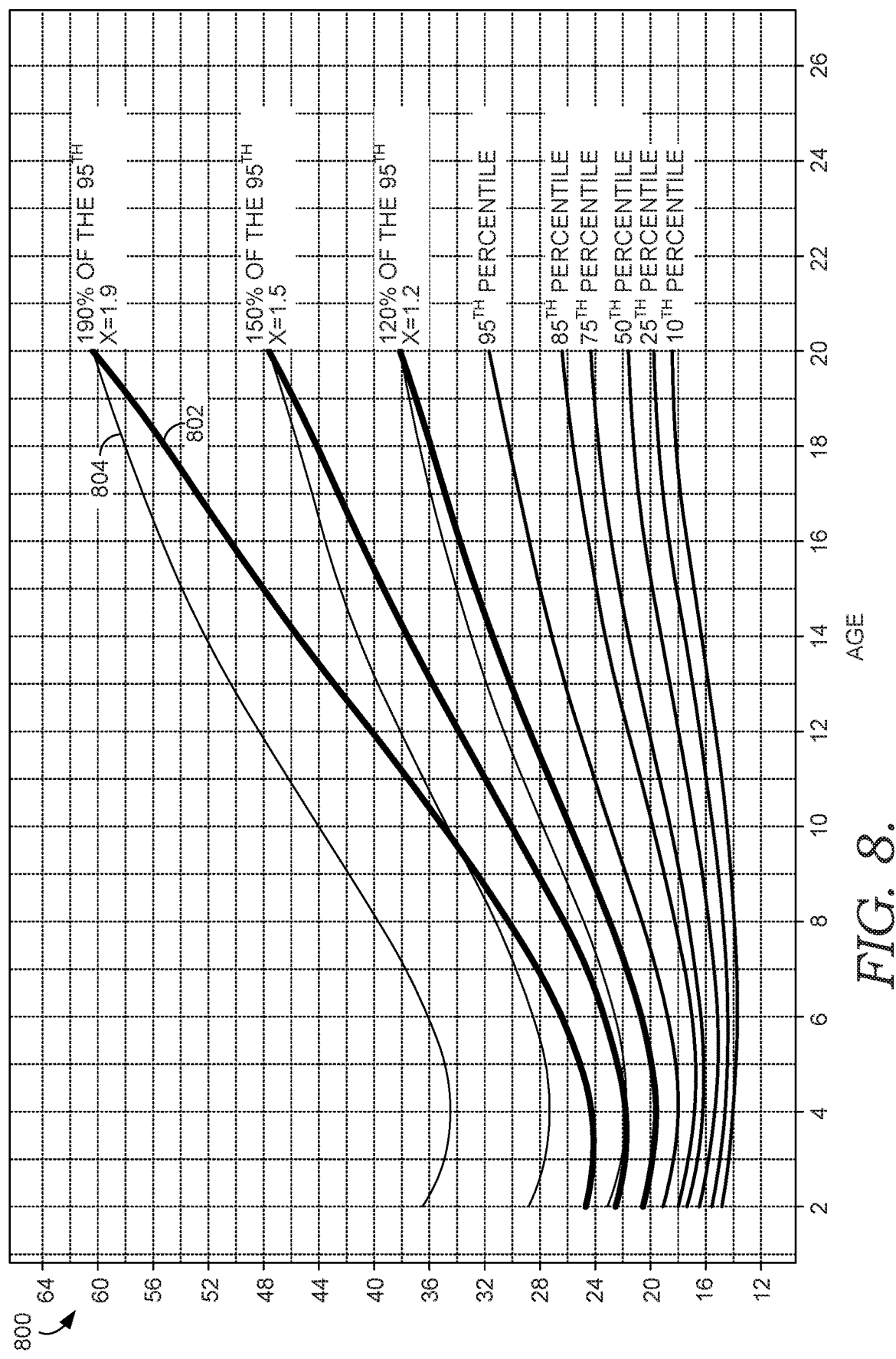
FIG. 8 depicts a graphical illustration comparing conventional pediatric obesity risk curves with pediatric obesity risk curves determined in accordance with an embodiment of the disclosure.

Turning to FIG. 8, a graphic illustration 800 of the curves formed using age-dependent multipliers overlaying with curves formed using the conventional approach of constant-multipliers is provided to further illustrate an improvement effected by of embodiments of the disclosure. In the graphic illustration 800, the $95^{th}$, $85^{th}$, $75^{th}$, $50^{th}$, $25^{th}$, and $10^{th}$ Percentile curves reflect traditional curves as defined by the CDC through the $95^{th}$ Percentile. The bold, thicker curves above the $95^{th}$ Percentile are extrapolations of the $95^{th}$ Percentile using age-dependent multipliers of 1.2, 1.5, and 1.9 in accordance with embodiments of the present disclosure. Curve 802, for example, is generated using the age-dependent multiplier described with respect to FIG. 5. The thinner curves above the $95^{th}$ Percentile (constant-multiplier curves) are based on constant-multipliers as discussed with respect to FIG. 5.

As illustrated in the graphic illustration 800, the age-dependent curves do not have as much variance in the younger age groups as the constant-multiplier curves. Accordingly, more severe obesity levels may be detected in younger pediatric populations using the age-dependent curves. Further, care plans and treatments may be more effectively determined using the age-dependent curves, since they more accurately detect obesity levels.

Returning to method 500 of FIG. 5, the one or more obesity risk curves may be used to assign an obesity risk level to a target patient. Accordingly, data for a target patient may be received, such as the patient's age and current BMI value. The target patient may be charted on the improved pediatric obesity chart 700 based on the age and BMI, and the obesity risk level may be assigned based on the location of where the target patient's data is plotted on the chart and one of the obesity risk curves. The obesity risk levels may be assigned in accordance with FIG. 7B above and as discussed further with respect to FIG. 10.

Figure 9A:
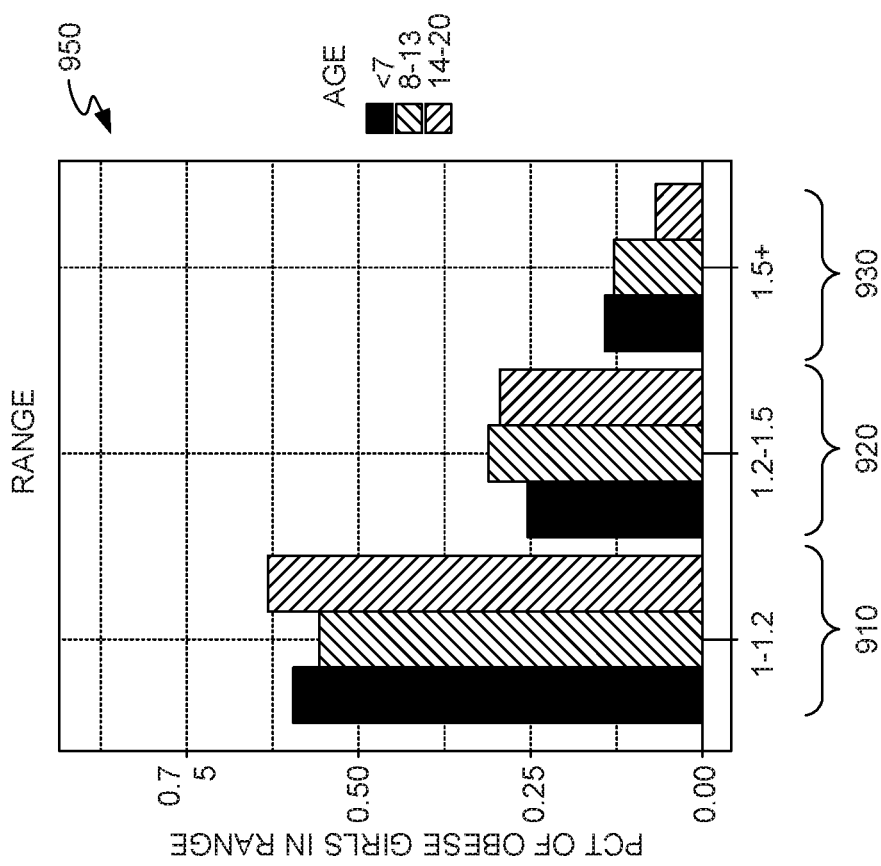
FIGS. 9A and 9B depict graphical illustrations of distributed obesity levels by age utilizing conventional obesity curves and obesity curves determined in accordance with an embodiment of the disclosure, respectively.
Figure 9B:
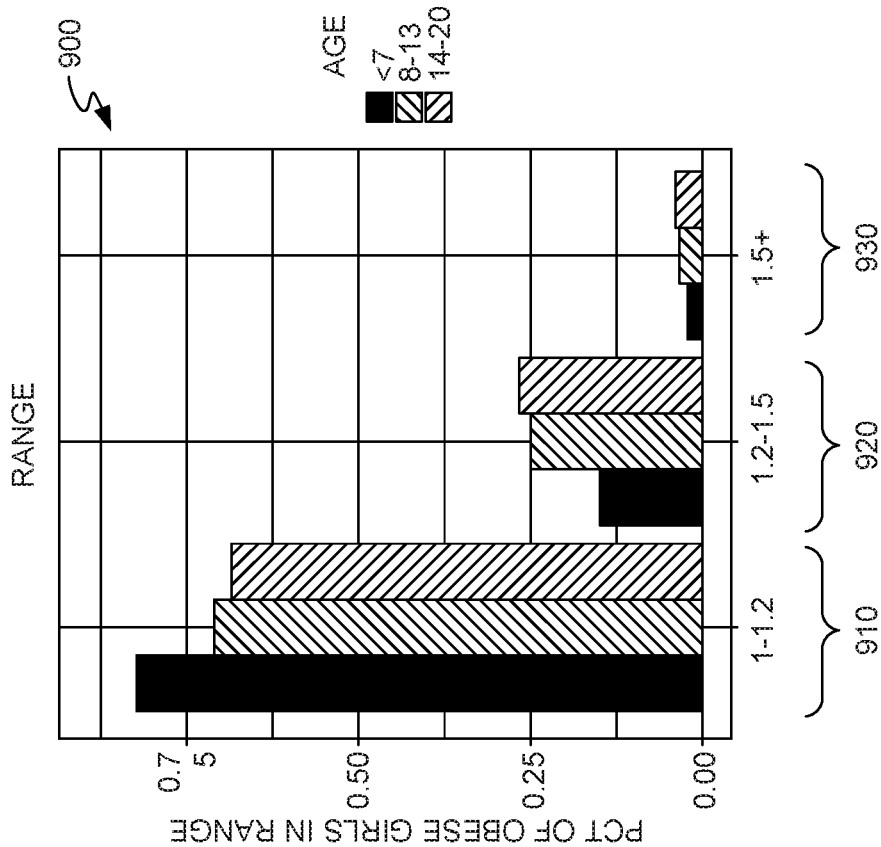

FIGS. 9A and 9B further illustrate the advantages of age-dependent risk stratification for pediatric obesity through bar charts indicating the proportions of the pediatric obese population in risk groups by age. Bar chart 900 in FIG. 9A depicts the distribution of obesity levels by age utilizing a conventional constant-multiplier approach, while bar chart 950 in FIG. 9B depicts the distribution of obesity levels by age utilizing age-dependent multipliers. Using the conventional approach, almost 85% of obese girls, age 7 and younger, fall into the lowest risk category 910 (x=(1–1.2)) and about 70% of the older girls (ages 14-20) fall into the lowest risk category 910. Relative to the bar chart 900 in FIG. 9A, the distribution in bar chart 950 in FIG. 9B-using risk groups based on age-dependent multipliers-places more children into the higher risk categories 962 (x=(1.2–1.5)) and 964 (x≥1.5). This effect on distribution is especially true for younger ages, such as seven years or younger. Accordingly, assigning obesity levels in accordance with the improved method of the present disclosure results in more children being accurately diagnosed with high obesity levels, which consequently leads to more successful intervention.

Figure 10:
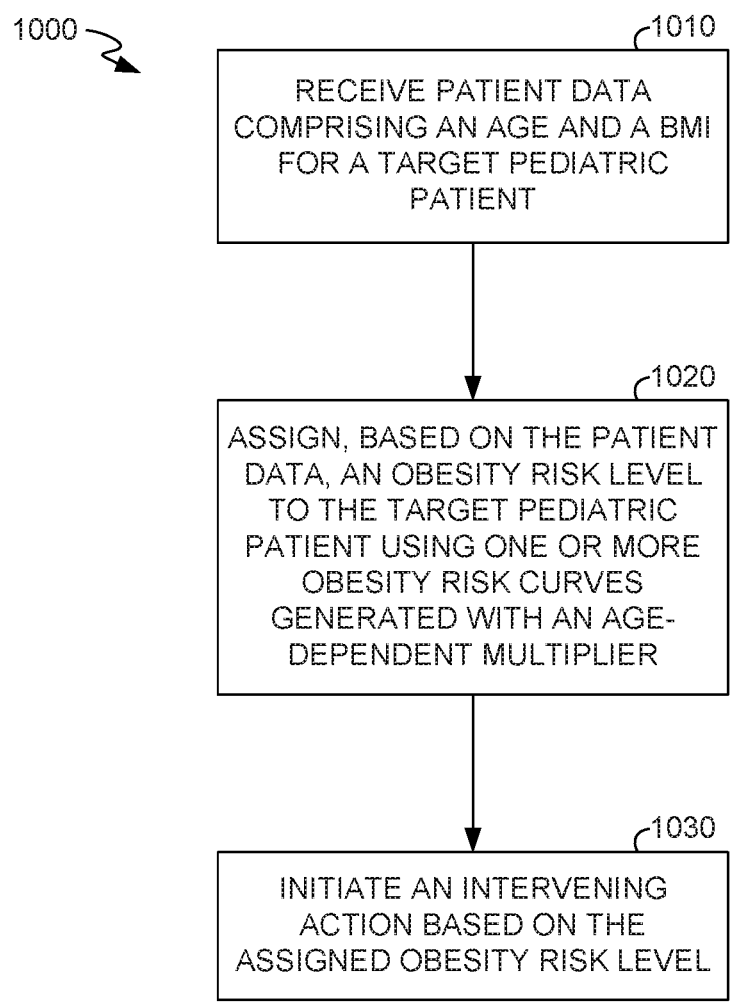
FIG. 10 depicts a flow diagram of a method for providing a decision support system for pediatric obesity, in accordance with an embodiment of the disclosure.

As previously stated, the obesity risk curves generated using an age-dependent multiplier may be used in a decision-support tool to provide intervening actions to a patient who is diagnosed as obese. FIG. 10 depicts a flow chart illustrating an example method 1000 for utilizing the improved obesity risk curves in a decision-support tool. In some aspects, method 1000 may be used in conjunction with method 500 of FIG. 5

At step 1010 in FIG. 10, patient data is received for a pediatric patient (who may also be referred to herein as a target pediatric patient). The patient data comprises indicators of the pediatric patient's age and BMI. Target pediatric patient data may also include other physiological variable measurements, such as height. Patient data may also include medical or social history and demographic information, for example. Additionally, the target pediatric patient data may be collected in many different ways, including, but not limited to, nurse recordings, remote devices, and other applications. Further, the target pediatric patient data may be fictional (e.g. for testing or calibration purposes) or may have already been recorded and stored in a database. The patient data for the target patient may be received in any of the manners described with respect to step 510 of FIG. 5.

At step 1020, an obesity risk level is assigned to the pediatric patient using one or more obesity risk curves generated with an age-dependent multiplier. The obesity risk curves may be curves that are generated using an age-dependent multiplier in accordance with method 500 of FIG. 5. As such, each curve may be created using an age-dependent multiplier that is formed with at least a growth velocity value and a risk threshold mount.

The obesity risk level assigned to the patient may indicate a degree to which the patient is obese. For example, the pediatric patient may be assigned an obesity risk level of "severe obesity," "morbid obesity," "super obesity" in addition to obesity. In this way, the one or more obesity risk curves assists a caregiver or healthcare provider to understand potential risks associated with a child's target pediatric patient data. Assigning an obesity risk level to the patient using the curves may comprise comparing the patient's BMI to a BMI level of the curve corresponding to the age of the patient, and the risk level may be assigned based on whether the patient's BMI meets or exceeds the threshold BMI level for the risk level as set by the obesity risk curve. For instance, a first obesity risk curve may set threshold BMI levels for a severely obese risk level, and where the patient's BMI is greater than the threshold BMI, the patient is assigned a severely obese risk level.

Utilizing age-dependent multipliers for risk stratification of obesity risk levels, more pediatric patients can be accurately determined to be in a higher obesity risk level (such as severe obesity and morbid obesity), and appropriate interventions may be undertaken. Accordingly, embodiments of this disclosure further include, at step 1030 of FIG. 10, comprise utilizing the determination of an obesity risk level based on age-dependent risk stratification to initiate an intervening action. One such intervening action may be a recommendation or notification that is emitted or otherwise communication to a caregiver responsible for the patient's care, such as a pediatrician. For instance, the obesity risk level may trigger a notification of the risk to be generated and communicated via a bedside alarm, user/clinician interface (such as interface 142 described in FIG. 1A), or may be communicated to a smartphone or personal computing device of a caregiver, thereby alerting the caregiver of a potential risk. Further, a graphic user interface with the pediatric growth chart with age-dependent-multiplier curves (such as the curves in FIG. 11C) may be provided on the user/clinician interface (such as interface 142). Additionally, some embodiments may comprise storing the result of the determination of the obesity risk level in an EHR associated with the patient and further may include providing the patient's EHR (or facilitating access to the EHR) in the notification.

In addition to or alternatively of the notification, a set of one or more actions relating to preventative and/or therapeutic responses may be initiated. For instance, the level of risk may be used to make provide a recommendation for intervening care plans corresponding to the level of risk. In some embodiments, more aggressive interventions, such as diets, activity plans, exercise schedules, and/or educational/awareness programs, may be recommended based on the obesity risk levels. Further interventions may include medications, procedures, and/or additional testing for clinical conditions likely to result from the determined obesity level or for underlying clinical conditions that may be attributing to the obesity. In some embodiments, the age and/or sex of the pediatric patient may also be used to determine the appropriate interventions. The recommendation may be provided in conjunction with a notification of the obesity risk level, and/or may be provided via a user/clinician interface, such as interface 142, described in connection with FIG. 1A.

Yet another action that may be initiated comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the obesity risk level determination.

A further action that may be initiated based on the determined obesity risk level comprising scheduling healthcare resources for the patient. For example in one embodiment, based on a higher obesity risk level (such as severe obesity and morbid obesity), it may be determined that a patient should see a dietician within a future time interval and, based on this determination, an appointment may be automatically scheduled, a referral to a dietician may be automatically made, and staff may be notified. In one embodiment, this action comprises modifying or updating a resource/scheduling electronic record in a resource/scheduling system.

Embodiments of this disclosure further include an improved user interface for facilitating diagnosing pediatric obesity. As previously mentioned, conventional obesity curves do not account for varying levels of obesity for children or, if they do, do not accurately capture higher risk levels of obesity in younger children. As such, conventional user interfaces based on these curves are unusable for diagnosing higher levels of pediatric obesity and providing appropriate and timely intervention.

Figure 11:
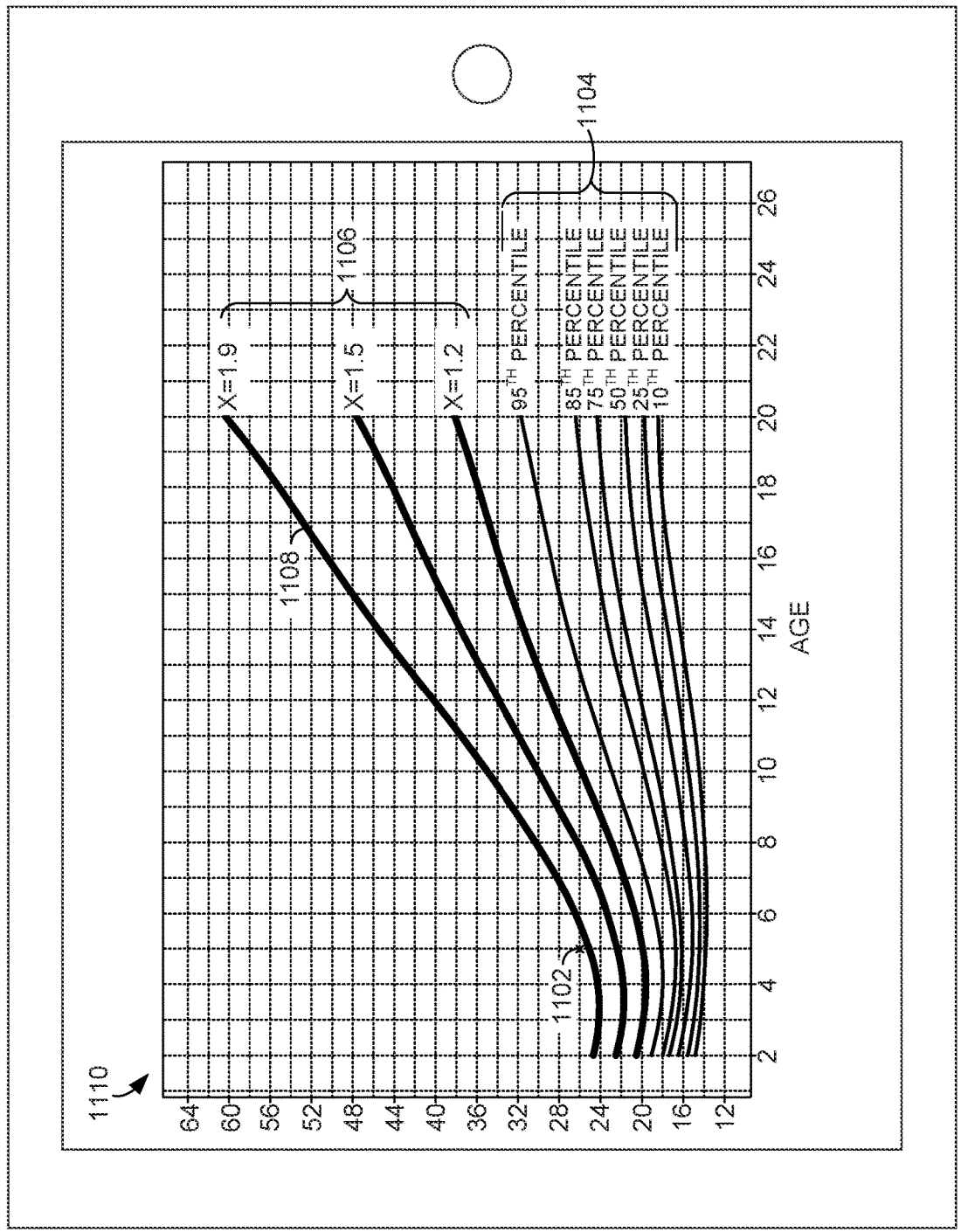
FIG. 11 depicts an aspect of a decision support tool comprising a user interface for facilitating diagnosing pediatric obesity in accordance with an embodiment of the disclosure.

In FIG. 11, for instance, depicts a computing device 1100 with a user interface 1110 generated in accordance with aspects of the present disclosure. User interface 1110 may be presented to a user, such as a pediatrician or caregiver, via a computerized display component of the computing device 1100. User interface 1110 includes a first set of curves 1104 reflecting percentiles for non-obese body types (e.g. healthy, underweight) and the 95th Percentile curve measuring a threshold for diagnosing obesity. In some aspects, the first set of curves 1104 for non-obese body types and the 95th Percentile curve may be generated using conventional methods, such methods utilizing only percentile thresholds for body type. User interface 1110 further includes a set of curves 1106 (also referred to herein as obesity risk curves) generated with an age-dependent multiplier in accordance with method 500.

In user interface 1110, a patient indicator 1102 is created and presented within the chart to reflect a particular patient's age and BMI value. In this example, the patient is 5 years old with a BMI of 26. When user interface 1110 combines patient indicator 1102 with the set of curves 1106 generated in accordance with embodiments of the present technology, patient indicator 1102 is positioned above obesity risk curve 1108 within the set of curves 1106. In some embodiments, obesity risk curve 1108 represents a threshold BMI for age for super obesity. As such, this interface 1110 may be used to assign the pediatric patient to a super obese category and appropriate intervention may be initiated for the patient.

When compared with conventional technologies, however, the patient would not have been accurately diagnosed. For instance, an interface created using only conventional percentiles, the patient would have been diagnosed as "obese" without an indicator of the severity of the obesity. Additionally, even with the conventional constant-multiplier approach, the patient would have only be diagnosed with severe obesity. Accordingly, the diagnosis of a higher level of obesity (i.e., super obese) in accordance with FIG. 11 may initiate more aggressive interventions that are more appropriate for treating the patient than would otherwise be provided with user interfaces generated according to conventional methods.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory media having instructions that, when executed by one or more processors, cause the one or more processors to facilitate a plurality of operations for providing intervention for pediatric obesity, the operations comprising:
receiving patient data for a pediatric patient, the patient data including an age and a body mass index (BMI) value of the pediatric patient;
assigning an obesity risk level to the pediatric patient based on the age and the BMI value of the pediatric patient,
wherein:
the obesity risk level is defined by one or more obesity risk curves that are each generated using an age-dependent multiplier,
the age-dependent multiplier is formed based at least in part on a growth velocity value,
the growth velocity value is determined based at least in part on reference information for a set of reference pediatric information, and
the reference information comprises data associated with one or both of an age indication and a BMI indication for each of a set of reference individuals within the set of reference pediatric information;
predicting, for each growth velocity value, for a plurality of ages, a proxy for obesity based on a reference pediatric population and based further on a machine-learning model,
wherein:
(a) the machine-learning model is trained by inputting, to the machine-learning model, proxy content corresponding to instances of information selected from a group comprising: (i) a health care spend amount for an individual in the reference pediatric population and (ii) at least one chronic condition, for the individual, from a set of chronic conditions associated with the reference pediatric population, and
(b) the predicting comprises applying, to the trained machine-learning model, data associated with at least a portion of the proxy content or the instances of information to generate a model output that facilitates the prediction of the proxy for obesity; and
wherein, based on the obesity risk level for the pediatric patient, one or more of (a) electronically notifying a caregiver, (b) recommending a treatment plan, (c) modifying a healthcare software program, or (d) scheduling a healthcare resource is initiated.

2. The one or more non-transitory media of claim 1, wherein the operations further comprise identifying an optimal growth velocity value based on at least the proxy for obesity.

3. The one or more non-transitory media of claim 2, wherein the optimal growth velocity value comprises one-third.

4. The one or more non-transitory media of claim 2, wherein the machine-learning model comprises a trained quantile regression model.

5. The one or more non-transitory media of claim 1, wherein the one or more obesity risk curves are generated using the age-dependent multiplier with a 95th percentile curve for BMI over age.

6. The one or more non-transitory media of claim 1, wherein an optimal growth velocity value is selected, from a set of growth velocity values, by: for each growth velocity value, predicting, for the plurality of ages, a health care spend amount for a patient in the reference pediatric population.

7. The one or more non-transitory media of claim 1, wherein the proxy for obesity includes at least a numerical value specifying a quantity of chronic conditions with which the individual has been diagnosed.

8. The one or more non-transitory media of claim 1, wherein:
the machine-learning model includes a machine-learning regression model, and
the operations further comprise updating the machine-learning regression model based on data associated with additional instances corresponding to the proxy content.

9. The one or more non-transitory media of claim 1, wherein the training is based at least in part on a process selected from a group comprising supervised machine learning, reinforcement machine learning, and unsupervised machine learning.

10. The one or more non-transitory media of claim 1, wherein a first age-dependent multiplier value corresponding to a first age differs from a second age-dependent multiplier value corresponding to a second age.

11. The one or more non-transitory media of claim 1, wherein a first growth velocity value corresponding to a first reference pediatric population differs from a second growth velocity value corresponding to a second reference pediatric population.

12. The one or more non-transitory media of claim 1, wherein a first risk level threshold value corresponding to a first age differs from a second risk level threshold value corresponding to a second age.

13. The one or more non-transitory media of claim 1, wherein the age-dependent multiplier differs with the age.

14. The one or more non-transitory media of claim 1, wherein each obesity risk curve is associated with a specific threshold risk value.

15. The one or more non-transitory media of claim 1, wherein applying the age-dependent multiplier to a first percentile obesity risk curve generates a different second percentile obesity risk curve than applying a constant multiplier to the first percentile obesity risk curve.

16. A computerized method for providing intervention for pediatric obesity, the method comprising:
receiving patient data for a pediatric patient, the patient data including an age and a body mass index (BMI) value of the pediatric patient;
assigning an obesity risk level to the pediatric patient based on the age and the BMI value of the pediatric patient,
wherein;
the obesity risk level is defined by one or more obesity risk curves that are each generated using an age-dependent multiplier,
the age-dependent multiplier is formed based at least in part on a growth velocity value,
the growth velocity value is determined based at least in part on reference information for a set of reference pediatric information, and
the reference information comprises data associated with one or both of an age indication and a BMI indication for each of a set of reference individuals within the set of reference pediatric information;
predicting, for each growth velocity value, for a plurality of ages, a proxy for obesity based on a reference pediatric population and based further on a machine-learning model,
wherein:
(a) the machine-learning model is trained by inputting, to the machine-learning model, proxy content corresponding to instances of information selected from a group comprising: (i) a health care spend amount for an individual in the reference pediatric population and (ii) at least one chronic condition, for the individual, from a set of chronic conditions associated with the reference pediatric population, and
(b) the predicting comprises applying, to the trained machine-learning model, data associated with at least a portion of the proxy content or the instances of information to generate a model output that facilitates the prediction of the proxy for obesity; and
wherein, based on the obesity risk level for the pediatric patient, one or more of (a) electronically notifying a caregiver, (b) recommending a treatment plan, (c) modifying a healthcare software program, or (d) scheduling a healthcare resource is initiated.

17. The computerized method of claim 16, further comprising:
selecting an optimal growth velocity value from a set of possible growth velocity values,
wherein selecting the optimal growth velocity value comprises:
receiving reference data for a particular reference pediatric population, the reference data comprising an age and a BMI value for each individual within the particular reference pediatric population;
for each possible growth velocity value within the set, normalizing BMI values from the reference data;
for each possible growth velocity value, predicting at least one health proxy for a plurality of ages; and
identifying the optimal growth velocity value based on the predicting of the at least one health proxy.

18. The computerized method of claim 17, wherein predicting of the at least one health proxy comprises applying a trained quantile regression model.

19. The computerized method of claim 17, wherein the optimal growth velocity value comprises a possible growth velocity value that minimizes dependence of age on the at least one health proxy.

20. The computerized method of claim 17, wherein the reference data further includes diagnoses of chronic conditions for individuals within the reference pediatric population.

21. The computerized method of claim 16, wherein the one or more obesity risk curves are generated using the age-dependent multiplier with a 95th percentile curve for BMI over age.

22. The computerized method of claim 16, wherein:
the predicting comprises applying the data to a machine-learning regression model, and
the proxy for obesity includes at least a numerical value specifying a quantity of chronic conditions associated with a patient in the reference pediatric population.

23. The computerized method of claim 16, wherein the computerized method is performed via one or more hardware processors associated with an electronic memory at a medical records computing system.

24. The computerized method of claim 16, wherein the computerized method is performed via parallel processors at different geographic locations associated with a distributed memory of a medical information computing system.

25. A computer system having one or more processors configured to facilitate a plurality of operations for providing intervention for pediatric obesity, the operations comprising:
receiving patient data for a pediatric patient, the patient data including an age and a body mass index (BMI) value of the pediatric patient;
assigning an obesity risk level to the pediatric patient based on the age and the BMI value of the pediatric patient,
wherein:
the obesity risk level is defined by one or more obesity risk curves that are each generated using an age-dependent multiplier,
the age-dependent multiplier is formed based at least in part on a growth velocity value,
the growth velocity value is determined based at least in part on reference information for a set of reference pediatric information, and
the reference information comprises data associated with one or both of an age indication and a BMI indication for each of a set of reference individuals within the set of reference pediatric information;

predicting, for each growth velocity value, for a plurality of ages, a proxy for obesity based on a reference pediatric population and based further on a machine-learning model, wherein:
(a) the machine-learning model is trained by inputting, to the machine-learning model, proxy content corresponding to instances of information selected from a group comprising: (i) a health care spend amount for an individual in the reference pediatric population and (ii) at least one chronic condition, for the individual, from a set of chronic conditions associated with the reference pediatric population, and
(b) the predicting comprises applying, to the trained machine-learning model, data associated with at least a portion of the proxy content or the instances of information to generate a model output that facilitates the prediction of the proxy for obesity; and wherein, based on the obesity risk level for the pediatric patient, one or more of (a) electronically notifying a caregiver, (b) recommending a treatment plan, (c) modifying a healthcare software program, or (d) scheduling a healthcare resource is initiated.

26. The computer system of claim 25, further comprising a computerized display component configured to present a set of curves indicating levels for non-obese body types for the reference pediatric population simultaneously with a set of the obesity risk curves.

27. The computer system of claim 26, wherein the set of curves indicating levels for non-obese body types is created without using the age-dependent multiplier.

28. The computer system of claim 26, wherein the computerized display component is further configured to present on a graphic user interface a target patient indicator based on a BMI value and an age of a target pediatric patient, the target patient indicator being presented with the set of obesity risk curves, and wherein the target pediatric patient is assigned to an obesity level based on a location of the target patient indicator relative to one or more obesity risk curves on the graphic user interface.

29. The computer system of claim 28, wherein the computerized display component is further configured to present a set of curves measuring BMI over age that is created without using the age-dependent multiplier, and wherein the obesity level cannot be assigned to the target pediatric patient using the set of curves indicating levels for non-obese body types.

30. The computer system of claim 25, wherein each obesity risk curve is generated using the age-dependent multiplier with a 95th percentile curve for BMI over age.

31. The computer system of claim 25, wherein a distance between two adjacent obesity risk curves at a first age is less than a distance between the two adjacent obesity risk curves at a second age that is greater than the first age.

32. The computer system of claim 25, wherein the predicting comprises: for each growth velocity value, for the plurality of ages, predicting a health care spend amount associated with a patient in the reference pediatric population.

33. The computer system of claim 25, wherein an optimal growth velocity value is determined based on: for each possible growth velocity value, predicting, for the plurality of ages, a health care spend amount for a patient in the reference pediatric population.

* * * * *